United States Patent [19]
Catania et al.

[11] 3,969,498
[45] July 13, 1976

[54] DRESSING AND METHOD FOR TREATING A WOUND

[75] Inventors: Patrick N. Catania; James C. King, both of Stockton, Calif.

[73] Assignee: University of the Pacific, Stockton, Calif.

[22] Filed: Sept. 13, 1973

[21] Appl. No.: 397,203

[52] U.S. Cl. ................................... 424/28; 424/45; 424/180; 424/DIG. 13
[51] Int. Cl.² .......................................... A61K 9/70
[58] Field of Search ............... 424/45, DIG. 13, 28, 424/180

[56] References Cited
UNITED STATES PATENTS

| | | | |
|---|---|---|---|
| 2,338,416 | 1/1944 | Fales | 424/DIG. 13 |
| 2,855,925 | 10/1958 | Novak | 424/28 |
| 2,876,165 | 3/1959 | Novak | 424/180 |
| 3,006,814 | 10/1961 | Stanko | 424/180 |
| 3,122,479 | 2/1964 | Smith | 424/180 |
| 3,238,100 | 3/1966 | Meyer et al. | 424/28 |
| 3,328,259 | 6/1967 | Anderson | 424/28 |
| 3,577,516 | 12/1969 | Gould et al. | 424/45 |

FOREIGN PATENTS OR APPLICATIONS

| | | | |
|---|---|---|---|
| 814,001 | 5/1959 | United Kingdom | 424/45 |
| 832,799 | 4/1960 | United Kingdom | 424/180 |

*Primary Examiner*—Frederick E. Waddell
*Attorney, Agent, or Firm*—Townsend and Townsend

[57] ABSTRACT

A wound dressing of the type having a water soluble plasma soluble self-supporting flexible body and which may be aerated and foamed. The flexible body is self-adhering to the wound tissues and forms an artificial eschar with the moist elements at the situs of the wound. The flexible body is formed primarily from a water soluble dextran polymer.

6 Claims, No Drawings

DRESSING AND METHOD FOR TREATING A WOUND

This invention relates to a dressing for a lesion or wound and a method for the use thereof in treating the same. More particularly it relates to dressings of the type having a water and plasma soluble flexible body that is capable of forming an artificial eschar with the exudates issuing from a lesion to which the dressing is applied. The dressing may contain medicaments or therapeutic agents for beneficially treating the wound. The dressing sequentially dissolves in the tissue of the wound, thereby sequentially releasing medicaments in the wound tissue.

U.S. Pat. No. 3,328,259 to Anderson, patented June 27, 1967, describes dressings of the type provided by the present invention. The dressings in the Anderson patent are stated to be water and plasma soluble and when applied to a wound are capable of forming an artificial eschar to protect the same while gradually dissolving and releasing therapeutic agents. As described in said patent such dressings have numerous advantages over previously used dressings. For example, ordinary gauze type dressings become incorporated into the granulation tissue at the surface of the lesion so that the new healthy tissue may be pulled off when the dressing is removed. Ordinary dressings are undesirably bulky, have to be changed at frequent intervals and cause an increase in maceration with subsequent prolongation of healing time. Occlusive dressings, such as creams, lotions, ointments and the like, must be rubbed into the open lesion thereby producing pain. Also, removal of occlusive materials is difficult. Such materials are generally not satisfactory because they do not permit air contact with wounds and like ordinary dressings cause an increase in maceration of the healing tissue.

In contrast to ordinary gauze type dressings and occlusive type dressings, the present flexible hydrophilic film is applied without inunction, is non-irritating to the lesion, is self-adhesive to the lesion, is easily removable by immersion for a few seconds in water or it may be left in place to be absorbed systemically and excreted by the body. While being absorbed, therapeutic agents or medicaments may be gradually released to the wound. The present type of dressing is thus a highly efficient dosage form for local therapy.

While the dressing provided by the Anderson patent, in common with the present dressing, provides many of these advantages over the older prior art, the principal component of the present dressing provides significant advantages over the materials used in the Anderson patent. Specifically the Anderson dressing is formed from certain water and plasma soluble cellulose derivatives. In the instant invention, the dressing is formed from water and plasma soluble dextran polymers in which the dextran is present in a sufficient amount to cause the flexible body formed therewith to form an artificial eschar with the moist elements at the situs of the wound. The dextran based flexible bodies of the present invention exhibit significant improvements in increased rates of solution in water and plasma in comparison with the flexible body dressings of the Anderson patent. For example, the Anderson dressings as disclosed in Example 4 of the Anderson patent require 1 minute and 10 seconds to dissolve in water. Dressings of the present invention are capable of dissolving in 30 seconds or less.

The dextran polymers of this invention are also advantageous in that they are generally available in a higher degree of purity than the cellulose materials of the prior art. Considering the application of the dressing produced therewith and the fact that it dissolves into the wound to be carried systemically points up the significance of such a fact. Along the same lines, the present dextran polymers are fully compatible with the human body and present substantially no question of toxicity or other potential health hazards. The cellulose materials of the prior art are not known to be completely free from any such complications. Moreover, the present materials have utility with all patients. The Anderson patent is not equally applicable to the extent that it suggests the use of sodium salts of celulose derivatives in the formation of its dressing. In certain instances the systemic incorporation of the sodium cellulose salts may introduce an undesirable excess of sodium in the body, taxing the body salt balance and inducing stress.

In the broad aspects of the present invention, the general considerations described in the Anderson patent are applicable except of course for the use of the instant dextran polymers instead of cellulose derivatives. In general the dextran polymer of the present invention will have an average molecular of about 40,000 to 100,000. For example, dressings made from specific dextran polymers having an average molecular weight of 40,000, 70,000 and 86,900 have been found to be satisfactory.

Preferably before use the formulation is reduced in moisture content so that the water is about 5–15% by weight of the dressing and the dextran polymer is about 60–90% by weight of the dressing thereby providing a solid self-supporting film-like material of suitable thickness. The dextran polymer is in an integral porous non-discrete form. The preferred form of the present body is as an aerated foam. This provides oxygen to the wound and also is more rapidly soluble compared with a non-foamed embodiment.

Where an aerated foam is the desired form, it is beneficial to include a surfactant in the formulation as a foaming agent. The surfactant also serves as an emulsifier. Such surfactant may be anionic, cationic, nonionic or amphoteric and is selected for its compatability and stability with the other components in the formulation. Examples of suitable surfactants are the ionic dioctyl sodium sulfosuccinate, the nonionic polyoxyethylene sorbitan monolaurate, and the amphoteric commercial material available under the name Miranol 2MCA Modified.

As before the film or body of the present invention may include antiseptics, steroids, germicidals, anesthetics, antibiotic materials and the like to minimize infection, pain and generally promote healing. Such materials are herein referred to generally as medicaments. Specifically it is contemplated to include mafenide or povidone iodine into the present dressing body or film. In other embodiments silver salts such as silver nitrate, silver sulfadiazine, gentamicin and salts thereof and local anesthetics such as lidocaine, benzocaine and salts thereof are specifically contemplated. Such medicaments are advantageously applied to wounds through the present dressing as distinguished from the dosage forms previously used therefor.

As before some residual moisture on the order of 5-15% by weight is desired so as to avoid a film that is either too brittle or too soft when outside of these limits. To this end plasticisers or humectants such as glycerin, sorbitol, propylene glycol and the like may be included in the formulation. Optional ingredients may include anti-oxidants and stabilizers for examples. Also consistent with prior procedures, the present dressing may be sterilized as with ethylene oxide, $CO_2$, or the like. Packaging is preferably in air proof and moisture proof material.

The following examples will illustrate the invention;

EXAMPLE 1

As a typical solution for the preparing of hydrophilic aerated dry films of this invention, take 16 grams of dextran AMW* 70,000 and dissolve it in 73.4 grams of water at 50°–70°C. To this solution, add 10.4 grams of sorbitol solution and 0.2 grams of Miranol 2MCA Modified. After whipping the film forming solution for 10–15 minutes, the resultant foam may be spread to a uniform depth onto a Teflon coated drying surface and dried at 50°–60°C to a moisture content of 5–15 percent. Such a film is aerated and one square inch thereof dissolves in 0.1 ml. of water at room temperature in less than 30 seconds.

*Average molecular weight

EXAMPLE 2

Take 20 grams of dextran AMW 86,900 and together with 8 grams of polyoxyethylene sorbitan monolaurate, 16 grams of glycerin, and an amount of mafenide acetate equivalent to 8.5 percent, by weight, of the dry film, and dissolve these in approximately 50 grams of water. After aerating the film forming solution by whipping with a mixer, the resultant foam is cast, dried, and cut to appropriate size.

EXAMPLE 3

Take 18 grams of dextran AMW 40,000, 10.4 grams of sorbitol solution, 1 gram of dioctyl sodium sulfosuccinate, and dissolve these in approximately 70 grams of water. In addition, silver salts, such as silver nitrate and silver sulfadiazine, may be added to the film forming solution to provide their therapeutic effects.

EXAMPLE 4

Composition of film forming solution:

|  | Gms. |
|---|---|
| Povidone Iodine | 2.4 |
| Preservative | 0.2 |
| Glycerin | 0.5 |
| Sorbitol Solution | 2.0 |
| Tween 20 | 1.0 |
| dextran AMW 86,900 | 77.9 |

Composition of aerated dry foam after casting and drying:

|  | Gms. |
|---|---|
| Povidone Iodine | 2.4 |
| Preservative | 0.2 |
| Glycerin | 0.5 |
| Sorbitol Solution | 2.0 |
| Tween 20 | 1.0 |
| dextran AMW 86,900 | 16.0 |
| Water | 2.4 |

EXAMPLE 5

|  | Gms. |
|---|---|
| Lidocaine Hydrochloride | 0.2 |
| dextran AMW 70,000 | 15.0 |
| Propylene Glycol | 8.0 |
| Alcohol | 10.0 |
| Water | 66.8 |

The above solution may be packaged in a pressurized aerosol utilizing suitable propellants. In this manner, the hydrophilic foam may be generated immediately prior to use by actuating the aerosol.

EXAMPLE 6

|  | Gms. |
|---|---|
| Dextran AMW 86,900 | 20.0 |
| Sorbitol Solution | 2.6 |
| Water | 77.4 |

The above film forming solution comprises a formulation to be used in preparing a non-aerated film for use as skin grafting material.

What is claimed is:

1. In a wound dressing of the type having a water soluble solid, self-supporting flexible body consisting essentially of a film-forming polymer in integral non-discrete form in an amount sufficient to form an artificial eschar with the moist elements at the situs of the wound, the improvement in which said film-forming polymer is a plasma and water soluble dextran polymer having an average molecular weight of about 40,000 to about 100,000.

2. The improvement in accordance with claim 1 wherein said dextran body is porous.

3. The improvement in accordance with claim 1 wherein said dextran polymer is about 60–90% by weight of said flexible body.

4. The improvement in accordance with claim 1 wherein said flexible body contains about 5–15% by weight of water.

5. The improvement in accordance with claim 1, wherein said flexible body contains medicaments preselected to treat the wound to be covered by said flexible body.

6. The improvement in accordance with claim 1 wherein said flexible body is in the form of an aerated foam.

* * * * *